(12) United States Patent
Kim et al.

(10) Patent No.: US 8,603,227 B2
(45) Date of Patent: Dec. 10, 2013

(54) COMPOSITION FOR PREVENTION OF INFLUENZA VIRAL INFECTION COMPRISING TANNIC ACID, AIR FILTER COMPRISING THE SAME AND AIR CLEANING DEVICE COMPRISING THE FILTER

(75) Inventors: Hyoung Joon Kim, Seoul (KR); Chan Jung Park, Seoul (KR)

(73) Assignee: Woongjin Coway Co., Ltd., Gongju-si (KR)

( * ) Notice: Subject to any disclaimer, the term of this patent is extended or adjusted under 35 U.S.C. 154(b) by 0 days.

(21) Appl. No.: 13/610,600

(22) Filed: Sep. 11, 2012

(65) Prior Publication Data

US 2013/0012461 A1     Jan. 10, 2013

Related U.S. Application Data

(63) Continuation of application No. 12/789,335, filed on May 27, 2010, now abandoned.

(60) Provisional application No. 61/252,327, filed on Oct. 16, 2009.

(51) Int. Cl.
*A61L 9/00* (2006.01)
*A61L 2/16* (2006.01)

(52) U.S. Cl.
USPC ....... 95/285; 96/226; 422/4; 422/28; 422/120

(58) Field of Classification Search
CPC .................................. B01D 39/00; B05D 1/18
USPC .......... 96/226; 422/28, 4, 120; 424/1.73, 400, 424/443; 427/384; 514/25; 536/18.2; 95/285
See application file for complete search history.

(56) References Cited

U.S. PATENT DOCUMENTS

| | | | | |
|---|---|---|---|---|
| 5,747,053 | A | * | 5/1998 | Nashimoto et al. ............ 424/405 |
| 5,783,502 | A | * | 7/1998 | Swanson ...................... 442/123 |
| 5,888,527 | A | * | 3/1999 | Nashimoto et al. ............ 424/405 |
| 7,727,915 | B2 | | 6/2010 | Skirius et al. |
| 2008/0022645 | A1 | | 1/2008 | Skirius et al. |
| 2008/0119545 | A1 | | 5/2008 | Hensley et al. |
| 2009/0019825 | A1 | | 1/2009 | Skirius et al. |
| 2009/0092624 | A1 | * | 4/2009 | Alberte et al. ............. 424/184.1 |
| 2009/0258074 | A1 | | 10/2009 | Hüffer et al. |
| 2009/0269378 | A1 | * | 10/2009 | Hueffer et al. ................ 424/402 |
| 2009/0275666 | A1 | | 11/2009 | Hueffer et al. |

FOREIGN PATENT DOCUMENTS

| | | |
|---|---|---|
| CN | 1452922 | 11/2003 |
| EP | 0 896 792 | 2/1999 |
| EP | 1 946 815 | 7/2008 |
| JP | 2009-539965 A | 11/2009 |
| JP | 2010-531362 A | 9/2010 |
| WO | 2007/131812 A1 | 11/2007 |
| WO | WO 2007131812 A1 * 11/2007 ............ B01D 39/00 |
| WO | 2007/144772 A2 | 12/2007 |
| WO | 2009/002516 A1 | 12/2008 |
| WO | 2010/067869 A1 | 6/2010 |

OTHER PUBLICATIONS

Ariaki Nagayama;"Inactivation of Influenza A Virus by Gentian Violet (GV) and GV-Dyed Cotton Cloth, and Bactericidal Activities of These Agents"; J Infect Chemother (2006) 12:73-79.*
Carson et al., "The Inactivation of Influenza Viruses by Tannic Acid and Related Compounds," *J. Bacteriol.* 66(5):572-575, 1953.
European Search Report, Dated May 4, 2011, for EP 10 00 5581, 8 pages.
Falbe et al. (eds.), *Römpp Chemie Lexikon*, Georg Thieme Verlag, Stuttgart, NY, 1995, pp. 4452-4453.
Nagayama, "Inactivation of influenza A virus by gentian violet (GV) and GV-dyed cotton cloth, and bactericidal activities of these agents," *J. Infect. Chemother.* 12:73-79, 2006.
Japanese Office Action, dated Jun. 14, 2012, for Japanese Application No. 2010-0805432, 6 pages. (English translation included).
*Nonwovens Review* 18(1):5-7, Jun. 2007. (Japanese language only).
Dawood et al., "Emergence of a Novel Swine-Origin Influenza A (H1N1) Virus in Humans," *N Engl J Med* 360(25):2605-2615, 2009.
Webster et al., "H5N1 Influenza—Continuing Evolution and Spread," *N Engl J Med* 355(21):2174-2177, 2006.
World Health Organization Publication, "Characteristics of the emergent influenza A (H1N1) viruses and recommendation for vaccine development," May 26, 2009, 6 pages.

* cited by examiner

*Primary Examiner* — Duane Smith
*Assistant Examiner* — Sonji Turner
(74) *Attorney, Agent, or Firm* — Seed IP Law Group PLLC

(57) ABSTRACT

Disclosed are a composition for the prophylaxis of influenza viral infection comprising tannic acid, an air filter coated with the same, and an air cleaner comprising the air filter. Having high inhibitory activity against influenza virus, the composition comprising tannic acid can be applied to the prevention of influenza viral infection. Also, the filter coated with the composition can remove influenza virus from the air so that it can be employed in an air cleaner for the prophylaxis of influenza viral infection.

8 Claims, No Drawings

COMPOSITION FOR PREVENTION OF INFLUENZA VIRAL INFECTION COMPRISING TANNIC ACID, AIR FILTER COMPRISING THE SAME AND AIR CLEANING DEVICE COMPRISING THE FILTER

CROSS-REFERENCE TO RELATED APPLICATIONS

This application is a continuation of U.S. patent application Ser. No. 12/789,335, filed May 27, 2010; which claims the benefit under 35 U.S.C. §119(e) of U.S. Provisional Patent Application No. 61/252,327, filed Oct. 16, 2009, which applications are incorporated herein by reference in their entirety.

BACKGROUND OF THE INVENTION

1. Field of the Invention

The present invention relates to a composition for the prophylaxis of influenza viral infection, comprising tannic acid, an air filter comprising the same, and an air cleaner comprising the air filter.

2. Description of the Related Art

Influenza, commonly referred to as the flu, is an infectious disease caused by RNA viruses of the family Orthomyxoviridae. The most common symptoms of the disease are chills, fever, sore throat, muscle pains, a severe headache, coughing, weakness/fatigue and general discomfort. Fever and coughing are the most frequent symptoms. In more serious cases, influenza causes complications which can be fatal.

Typically, influenza is transmitted through the air by coughs or sneezes, creating aerosols containing the virus. Influenza can also be transmitted by direct contact with bird droppings or nasal secretions, or through contact with contaminated surfaces. Airborne aerosols have been thought to cause most infections, although the most important means of transmission is not absolutely clear. Influenza viruses can be inactivated by sunlight, disinfectants and detergents. As the virus can be inactivated by soap, frequent hand washing reduces the risk of infection.

Influenza spreads around the world in seasonal epidemics, resulting in the deaths of between thousands and tens of thousands of people every year, up to millions in some pandemic years. Three influenza pandemics occurred in the $20^{th}$ century and killed tens of millions of people, with each of these pandemics being caused by the appearance of a new strain of the virus in humans. Often, these new strains appear when an existing flu virus spreads to humans from another animal species, or when an existing human strain picks up new genes from a virus that usually infects birds or pigs. An avian strain named H5N1 raised the concerns of a new influenza pandemic, after it emerged in Asia in the 1990s, but it has not evolved into a form that spreads easily from human to human. In April 2009, a novel flu strain, known as influenza A/H1N1, emerged in Mexico and spread over many other nations.

In terms of virus classification, influenza viruses are RNA viruses that make up three (influenzavirus A, influenzavirus B and influenzavirus C) of the five genera of the family Orthomyxoviridae.

The genus Influenzavirus A has one species, influenza A virus. Wild aquatic birds are the natural hosts for a large variety of influenza A. Occasionally, viruses are transmitted from one to another species and may then cause devastating outbreaks or give rise to influenza pandemics. Type A viruses are the most virulent human pathogens among the three influenza types. The influenza A virus can be subdivided into different serotypes (subtypes) based on the antibody response to these viruses. The serotypes that have been confirmed in humans, ordered by the number of known human pandemic deaths, are as follows: first, H1N1 caused the Spanish flu in 1918, and the 2009 flu pandemic. H2N2 caused the Asian Flu in 1957 and H3N2 caused the Hong Kong Flu in 1968. In addition, H5N1, H7N7, H1N2, H9N2, H7N2, H7N3, and H10N7 appeared.

A more detailed description will now be given of H1N1. Influenza A (H1N1) virus (influenza A virus subtype H1N1) or simply H1N1 is the most common cause of human influenza. In addition, this subtype can infect pigs and birds.

A variant of H1N1 was responsible for the Spanish flu pandemic that killed some 50 to 100 million people worldwide over about a year in 1918 and 1919. The H1N1 genome was published in the journal of Science in 2005, reporting "When compared with today's human flu viruses, the 1918 virus had alterations in just 25 to 30 of the virus's 4,400 amino acids." Low pathogenic H1N1 strains still exist in the wild today, causing roughly half of all flu infections in 2006.

From March of 2009, the worldwide death toll from the H1N1 virus increased. The influenza was first dubbed swine flu, but renamed as a new flu or as the new influenza A (H1N1) in Korea because the influenza A virus subtype H1N1 cannot be spread by eating pork or pork products. The World Health Organization (WHO) officially declared the outbreak to be a pandemic on Jun. 11, 2009.

According to government statistical data, more than ten thousand cases of the new flu were generated with eight serious cases hospitalized and 14 patients dying from chronic or acute complications, as of Sep. 16, 2009.

The genus Influenzavirus B has one species, influenza B virus. Influenza B almost exclusively infects humans and is less common than influenza A. The only other animals known to be susceptible to influenza B infection are the seal and the ferret. This type of influenza mutates at a rate 2-3 times slower than type A and consequently is less genetically diverse, with only one influenza B serotype. As a result of this lack of antigenic diversity, influenza B almost never causes the outbreak of a pandemic because of its limited host range.

The genus Influenzavirus C has one species, influenza C virus, to which humans, dogs and pigs are susceptible. Influenza C is less common than the other types A and B and usually only causes mild disease in children.

Among antiviral drugs currently available for the treatment of influenza are oseltamivir (trade name: Tamiflu), zanamivir (trade name: Relenza), peramivir and amantadine, with the predominant application of Tamiflu to the treatment of influenza A virus subtype H1N1. Tamiflu, a drug with a worldwide monopoly, was developed to treat avian influenza (AI). By blocking the activity of the viral neuraminidase enzyme, Tamiflu prevents new viral particles from being released by infected cells. An effective efficacy can be obtained when it is taken within 48 hours of the onset of symptoms. The main efficacy of Tamiflu is known to lie in the relief of symptoms, the warding off of secondary complications such as bronchitis or pneumonia, and a decrease of the latent period. Tamiflu has been used to treat and prevent influenzavirus A and influenzavirus B infections in tens of millions of people since 1999. Zanamivir, sold under the trade name of Relenza, is a neuraminidase inhibitor used in the treatment and prophylaxis of Influenzavirus A and Influenzavirus B.

Side effects associated with oseltamivir therapy include nausea and vomiting. Zanamivir shows high antiviral effects, but poor bioavailability, with fast release from the kidney.

Most of the anti-influenza agents developed thus far have side effects. Thus, there is the need for the development of an anti-influenza composition that is effective for the treatment and prophylaxis of influenza viral infection.

Commonly, influenza is spread via the airborne route, that is, when someone inhales the aerosols produced by the coughing, sneezing or spitting of an infected person. Influenza can also be spread by direct transmission, e.g., by way of the excretions, spit, snivel, or blood of infected persons. However, the spread of influenza results mostly from droplet infection such as by aerosol inhalation. Influenza viruses may be inactivated by sunlight, disinfectants, surfactants, e.g., soap, which are however not effective for the removal of airborne viruses.

The capture and inactivation of airborne viruses may lead to the effective prevention of influenza infection.

An air filter is an air-permeable member which can removes solid particulates from the air. Air filters are used in applications where air quality is important, such as in air cleaners, air conditioners, vacuum cleaners, humidifiers, dehumidifiers, etc., notably in building ventilation systems and in engines.

Designed to remove contaminants from the air, an air cleaner comprises a plurality of filters composed typically of a pretreatment filter for removing large size particles; a deodorizing filter for removing odor, volatile organic chemicals, formaldehyde, etc.; an HEPA filter for removing airborne particulates which have a diameter on the micrometer scale; and a median filter, arranged in front of the HEPA filter, for protecting the HEPA filter.

More filters may result in higher air-purifying performance, but increase resistance against overall air circulation. Accordingly, 3 to 5 filters are typically employed in an air cleaner.

Recently, studies have focused on functional filters which can selectively remove harmful materials in an elaborate manner or substitute beneficial materials for harmful materials. For example, filters for removing microparticulates with high efficiency or for purifying the airborne particulates which cause sick house syndrome have been developed.

Leading to the present invention, intensive and thorough research into a composition acting against new influenza A H1N1, conducted by the present inventors, resulted in the finding that a sumac extract has an inhibitory activity against influenza viruses and that a composition comprising tannic acid as an active ingredient is useful in the prophylaxis of influenza viral infection and a filter coated with the extract can effectively remove airborne influenza viruses.

SUMMARY OF THE INVENTION

It is therefore an object of the present invention to provide a composition for the prevention of influenza viral infection, comprising tannic acid.

It is another object of the present invention to provide an air filter comprising the composition.

It is a further object of the present invention to provide an air cleaner comprising the filter.

In accordance with an aspect thereof, the present invention provides a composition for the prevention of influenza viral infection, comprising tannic acid as an active ingredient.

In a preferred embodiment, the composition may be applied to quasi-drugs.

In accordance with another aspect thereof, the present invention provides an air filter comprising the composition.

It accordance with a further aspect thereof, the present invention provides an air cleaner comprising the air filter.

DESCRIPTION OF THE PREFERRED EMBODIMENTS

The present invention addresses a composition for the prophylaxis of influenza viral infection, comprising tannic acid as an active ingredient As used herein, the term "prevention" or "prophylaxis" is intended to include all actions suppressing influenza viral infection or deterring the outbreak of influenza.

In the present invention, the influenza virus may be directed into influenza A virus, influenza B virus or influenza C virus, with a preference for influenza A virus and a higher preference for new influenza A (H1N1) virus.

Influenza A (H1N1) virus is a subtype of influenza A virus and is the most common cause of influenza (flu) in humans. Some strains of H1N1 are endemic to pigs (swine influenza) and to birds (avian influenza). Examples of the influenza A include A/PR/8(H1N1), A/WSN/33(H1N1), A/Bervig-Mission/1/18(rvH1N1), and A/Singapore/6/86(H1N1).

Among the new influenza A (H1N1) virus, which is responsible for the 2009 flu pandemic, are A/California/O4/09 and A/California/7/2009.

When infected with a new influenza A (H1N1) virus, patients suffer from fever, coughing, sore throat, bronchitis, pneumonia, etc. The virus may cause an outbreak of avian flu, swine flu or goat flu.

Tannic acid has a molecular formula of $C_{76}H_{52}O_{46}$ with a molecular weight of 701.23, represented by the following Chemical Formula 1:

−continued

Tannic acid may be purchased commercially or taken from plants.

For use in the present invention, tannic acid may be in the form of pharmaceutically acceptable salts. Useful are acid addition salts with pharmaceutically acceptable free acids. Acid addition salts may be obtained with inorganic acids such as hydrochloric acid, nitric acid, phosphoric acid, sulfuric acid, hydrobromic acid, hydroiodic acid, nitrous acid, phosphorous acid, etc., or non-toxic organic acids such as aliphatic mono- and dicarboxylate, phenyl-substituted alkanoate, hydroxy alkanoate and alkanedioate, aromatic acids, aliphatic and aromatic sulfonic acids. Examples of the pharmaceutically acceptable salts include sulfate, pyrosulfate, bisulfate, sulfite, bisulfate, nitrate, phosphate, monohydrogen phosphate, dihydrogen phosphate, metaphosphate, pyrophosphate chloride, bromide, iodide, fluoride, acetate, pyropionate, decanoate, caprylate, acrylate, formate, isobutyrate, caprate, heptanoate, propiolate, oxalate, malonate, succinate, suberate, sebacate, fumarate, maleate, butyn-1,4-dioate, hexan-1,6-dioate, benzoate, chlorobenzoate, methylbenzoate, dinitrobenzoate, hydroxybenzoate, methoxybenzoate, phthalate, terephthalate, benzensulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, metanesulfonate, propanesulfonate, naphthalene-1-sulfonate, naphthalene-2-sulfonate and mandelate.

The acid addition salts useful in the present invention may be prepared using a typical method, for example by dissolving the compound in excess an aqueous acid solution and precipitating with a water-miscible organic solvent, such as methanol, ethanol, acetone or acetonitrile.

Also, tannic acid may be in the form of pharmaceutically acceptable metal salts. For this, alkaline metal or alkali earth metal may be employed. For example, the compound is dissolved in excess alkaline metal hydroxide or alkali earth metal hydroxide and the residue is filtered off. The filtrate is evaporated and dried to afford a desired salt. Pharmaceutically suitable are sodium, potassium or calcium salts. Additionally, corresponding silver salts may be obtained by reacting proper silver salts (e.g., silver nitrate) with alkaline metal or alkali earth metal.

In accordance with another embodiment of the present invention, the composition for the prophylaxis of influenza viral infection may be applied to quasi-drugs.

With the aim of preventing infection with an influenza virus, the composition of the present invention may be used as an additive in a quasi-drug. In this regard, the composition may be used alone or in combination with another quasi-drug or ingredient in a typical manner. The amount of the composition in the quasi-drug may be determined depending on the purpose thereof.

Examples of the quasi-drug to which the composition of the present invention may be applied include a filter coating, a hand-wash, a mouthwash, a disinfectant, a shower foam, a water tissue, a detergent soap, a humidifier filler, a mask, and an aromatic.

In accordance with a further embodiment thereof, the present invention addresses an air filter comprising the composition for the prophylaxis of an influenza viral infection.

The term "air filter", as used herein, refers to a filter which functions to remove airborne microorganisms and dust and which prevents secondary contamination attributable to a filter. The air filter of the present invention may be thus applied to automobile cabins, household electric appliances, air conditioning systems, gas masks, air cleaners, and clean rooms, with a preference for air cleaners.

Further, the present invention addresses a method for manufacturing the air filter comprising the composition for the prophylaxis of influenza viral infection. The method is described below.

The method for manufacturing an air filter comprising a composition for the prophylaxis of influenzavirus infection comprises:

(a) preparing the composition for the prophylaxis of influenza viral infection;

(b) coating the air filter with the composition for the prophylaxis of an influenza viral infection; and (c) drying the coated filter.

Step (b) may be conducted by a process of immersing a roller in the composition for the prophylaxis of influenza viral infection and applying the roller to the filter base, a process of immersing a filter base in combination with a roller in the composition for the prophylaxis of influenza viral infection, and/or a process of spraying a filter base with the composition for the prophylaxis of influenza viral infection.

As the filter base, a metal, a plastic, a non-woven fabric, or a film may be used. Highly porous non-woven fabrics are preferably used in air filters for air cleaners.

Examples of the plastic include, but are not limited to, polypropylene, polyethylene, polyurethane, acryl, PVC and polystyrene, with a preference for polypropylene.

Nonwoven fabric is a sheet-like material made from long fibers, bonded together by chemical, mechanical, heat or solvent treatment. It may be divided into paper-based and fiber-based nonwoven fabric depending on the base material thereof. Examples of the nonwoven fabric material useful in the present invention include rayon, lyocell, and polypropylene, but are not limited thereto. As long as it is well known in the art, any nonwoven fabric material may be used. Preferable is polypropylene.

When taken as a filter base, a plastic resin may be melted and spun to produce filaments which are then weaved to a cloth or formed into webs, followed by binding them together into nonwoven fabric. Further, a foaming agent may be used to form a porous filter.

Above all, a composition for the prophylaxis of influenza viral infection is first prepared. Once prepared, the composition for the prophylaxis of influenza viral infection may be dissolved or diluted in a certain solvent so that it can be used in the manufacture of the air filter. The solvent may be selected from among water, ethanol, methanol, butanol, n-hexane, n-heptane, DMSO and a combination thereof.

The composition for the prophylaxis of influenza viral infection is applied to a filter base. To this end, a roller mounted with an absorbent member such as a sponge may be immersed in the composition and rolled along the filter base, followed by drying the filter base. Alternatively, the filter base may be directly immersed in the composition and dried. In another alternative, the filter base may be sprayed with the composition and dried.

The coating process may be conducted before as well as after the fibers are weaved into a filter base. In the former case, the fibers may be coated with the composition by immersing or spraying, after which they may be weaved into a filter base.

After being coated with the composition by immersing or spraying, the filter may be dried at room temperature or with hot wind. As long as it is well known in the art, any drying method may be employed without limitations. Because drying causes the composition to be well absorbed therein, the filter can have inhibitory activity against influenza virus for a long period of time.

In addition to the composition of the present invention, the filter according to the present invention may comprise a conventional antibacterial agent, a deodorant (e.g., a flavonoid, phytoncide, pyroligneous liquor, a plant extract, cyclodextrin, metal ion, or titanium dioxide), a dust collecting agent, etc. These agents may be applied individually or in combination, with no particular limitations imparted to the order of coating.

In accordance with a further embodiment thereof, the present invention addresses an air cleaner equipped with the air filter.

As mentioned above, an air cleaner comprises a plurality of filters. The air filter comprising the composition for the prophylaxis of influenza viral infection can be employed as a functional filter in the air cleaner.

No limitations are imparted to the type of the air cleaner to which the air filter of the present invention is applied. It may be applied to air cleaners for home, offices, and automobile cabins. Of course, the air cleaner may comprise known typical constitutional factors. Preferably, the air cleaner of the present invention comprises an air filter placed between an air intake and an air exhaust.

In accordance with still another embodiment thereof, the present invention addresses a method for purifying air using the air cleaner.

A better understanding of the present invention may be obtained through the following examples which are set forth to illustrate, but are not to be construed as limiting the present invention.

Preparation Example 1

Manufacture of an Air Filter Coated with Tannic Acid

Tannic acid (A&K Petrochem, Ontario, Canada) was added in an amount of 10 wt % to water to give a tannic acid solution. This solution was sprayed onto a polypropylene filter base which was then dried at 140° C. for 4 min.

Experimental Example 1

Assay for Inhibitory Activity of Tannic Acid Against Influenza Virus

Tannic acid was assayed for inhibitory activity against influenza virus as follows.

As influenza virus strains to be tested, influenza A subtype H1N1 viruses A/PR/8 (H1N1) and A/WSN (H1N1) as well as the WHO standard strain influenza A (H1N1) (A/California/O4/09), which was responsible for the declaration of the 2009 pandemic, were used.

Tannic acid was used as a sample in the following procedure.

The MDCK (Mardine Darbine Canine Kidney) cell line was inoculated at a density of $1.5 \times 10^6$ cells/mL into 6-well plates which were then incubated at 37° C. for 24 his in a 5% $CO_2$ atmosphere. Separately, tannic acid was diluted to 100 mg/ml (1×) in an injection solution. The dilution was subjected to serial 10-fold dilutions. The specimens thus obtained were added in an amount of 90 µL per well to 96-well plates. 10 uL of an influenza virus sample was added to each well, incubated for 10 min, and 10-fold diluted with PBS. The MDCK cell line which had grown to confluence on the plates was infected with 1 mL of the dilution and incubated for 1 hr. For an "infection+non-administration" control, the MDCK cell line was infected with influenza virus which had not been treated with tannic acid.

Thereafter, the medium was removed, and a mixture of 1:1 2× agarose:2×MEM containing 10 µg/ml trypsin was added in an amount of 2 mL per well. The MDCK cells were incubated at 37° C. for 2 days, fixed with 1 mL of 4% paraformaldehyde, and washed with water to remove agarose. On the next day, the cells were stained with crystal violet to count plaques and express the titer as plaque forming unit (pfu)/mL. The results are summarized in Tables 1 to 3, below.

$$\text{Inhibitory Activity}(\%) = (1 - \text{Tannic Acid-Treated Group/Control}) \times 100 \qquad [\text{Equation 1}]$$

TABLE 1

TITER OF NEW INFLUENZA A (H1N1) (A/CALIFORNIA/O4/09) AFTER TREATMENT WITH SAMPLE

| Sample | Virus Titer (pfu/ml) | Inhibitory Activity (%) |
|---|---|---|
| Control | $1.9 \times 10^6$ | — |
| Tannic Acid | Not-detected | 99.99 |

TABLE 2

TITER OF INFLUENZA A/WSN/33 (H1N1) AFTER TREATMENT WITH SAMPLE

| Sample | Virus Titer (pfu/ml) | Inhibitory Activity (%) |
|---|---|---|
| Control | $3.4 \times 10^8$ | — |
| Tannic Acid | Not-detected | 99.99 |

TABLE 3

TITER OF INFLUENZA A/PR/8 (H1N1) AFTER TREATMENT WITH SAMPLE

| Sample | Virus Titer (pfu/ml) | Inhibitory Activity (%) |
|---|---|---|
| Control | $3.9 \times 10^9$ | — |
| Tannic Acid | Not-detected | 99.99 |

As is apparent from the data of Tables 1 to 3, the groups treated with tannic acid were significantly reduced in virus count compared to the control, indicating that tannic acid has excellent inhibitory activity against influenza virus.

Experimental Example 2

Assay for Inhibitory Activity of the Air Filter Against Influenza Virus

The air filters coated with tannic acid, manufactured in Preparation Example 1, were assayed for inhibitory activity against the influenza virus as follows.

As influenza virus strains to be tested, influenza A subtype H1N1 viruses A/PR/8 (H1N1) and A/WSN(H1N1) as well as the WHO standard strain influenza A (H1N1) (A/California/O4/09), which was responsible for the declaration of the 2009 pandemic were used.

The air filters manufactured in Preparation Example 1 were used as samples. For control, an air filter was not treated with tannic acid.

After being cut into a size of 2×2 cm, the filter was coated with a predetermined amount of the virus solution and incubated for 10 min so as to absorb the virus thereinto. A medium (1 mL) was loaded onto the filter which was then shaken for 10 min to wash off the virus. The filtrate was diluted to prepare specimens. 90 µL of each of the specimens was added, together with 10 µL of influenza virus, to each well of 96-well plates, followed by incubation for 10 min and 10-fold dilution with PBS. The MDCK cell line grown to confluence on the plates was infected with 1 mL of the dilution and incubated for 1 hrs. For an "infection+non-administration" control, the MDCK cell line was infected with influenza virus which had not been treated with tannic acid.

Thereafter, the medium was removed, and a mixture of 1:1 2× agarose:2×MEM containing 10 µg/ml trypsin was added in an amount of 2 mL per well. The MDCK cells were incubated at 37° C. for 2 days, fixed with 1 mL of 4% paraformaldehyde, and washed with water to remove agarose. On the next day, the cells were stained with crystal violet to count plaques and express the titer as plaque forming unit (pfu)/mL. The results are summarized in Tables 4 to 6, below.

TABLE 4

TITER OF NEW INFLUENZA A(H1N1) (A/CALIFORNIA/O4/09) AFTER TREATMENT WITH SAMPLE

| Sample | Virus Titer (pfu/ml) | Inhibitory Activity (%) |
|---|---|---|
| Control | $1.9 \times 10^6$ | — |
| Air Filter Treated with Tannic Acid | Not-detected | 99.99 |

TABLE 5

TITER OF INFLUENZA A/WSN/33 (H1N1) AFTER TREATMENT WITH SAMPLE

| Sample | Virus Titer (pfu/ml) | Inhibitory Activity (%) |
|---|---|---|
| Control | $3.4 \times 10^8$ | — |
| Air Filter Treated with Tannic Acid | Not-detected | 99.99 |

TABLE 6

TITER OF INFLUENZA A/PR/8 (H1N1) AFTER TREATMENT WITH SAMPLE

| Sample | Virus Titer (pfu/ml) | Inhibitory Activity (%) |
|---|---|---|
| Control | $3.9 \times 10^9$ | — |
| Air Filter Treated with Tannic Acid | Not-detected | 99.99 |

The data of Tables 4 to 6 demonstrate that the air filter treated with tannic acid has excellent inhibitory activity against influenza virus.

Having high inhibitory activity against influenza virus, as described hitherto, the composition comprising tannic acid in accordance with the present invention can be applied to the prevention of influenza viral infection. Hence, a filter coated with the composition can remove influenza virus from the air so that it can be employed in an air cleaner for the prophylaxis of new influenza viral infection.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for inactivating an influenza A (H1N1) virus in vitro, comprising treating the influenza A (H1N1) virus with a composition comprising tannic acid, wherein the influenza virus is A/California/04/09.

2. The method according to claim 1, wherein the composition is used in preparing a filter coating agent, a hand-wash, a mouthwash, a disinfectant, a shower foam, a water tissue, a detergent soap, a humidifier filler, a mask, or an aromatic.

3. The method according to claim 1, wherein the composition is used in preparing an air filter.

4. A method for inactivating an influenza A (H1N1) virus in vitro, comprising treating the influenza A (H1N1) virus with an air filter comprising a composition comprising tannic acid, wherein the influenza virus is A/California/04/09.

5. The method according to claim 4, wherein the air filter comprises a filter base, wherein the filter base is plastic or nonwoven fabric.

6. The method according to claim 5, wherein the nonwoven fabric is paper-based nonwoven fabric or fiber-based nonwoven fabric.

7. The method according to claim 4, wherein the air filter is provided in an air cleaner.

8. A method for inactivating an influenza A (H1N1) virus in vitro, comprising treating the influenza A (H1N1) virus with an air cleaner comprising an air filter comprising a composition comprising tannic acid, wherein the influenza virus is A/California/04/09.

\* \* \* \* \*